United States Patent
Lee

(10) Patent No.: US 8,481,761 B2
(45) Date of Patent: Jul. 9, 2013

(54) METHOD FOR PREPARING SESAMIN AND SESAMOLIN

(75) Inventor: Min-Hsiung Lee, Wugu Township (TW)

(73) Assignee: Foreway Biotech Inc., Wugu Township (TW)

( * ) Notice: Subject to any disclaimer, the term of this patent is extended or adjusted under 35 U.S.C. 154(b) by 405 days.

(21) Appl. No.: 12/579,888

(22) Filed: Oct. 15, 2009

(65) Prior Publication Data

US 2011/0004008 A1 Jan. 6, 2011

(30) Foreign Application Priority Data

Jul. 1, 2009 (TW) .............................. 98122194 A

(51) Int. Cl.
*C07D 317/44* (2006.01)
(52) U.S. Cl.
USPC ........................................................ 549/445
(58) Field of Classification Search
USPC ........................................................ 549/445
See application file for complete search history.

(56) References Cited

U.S. PATENT DOCUMENTS

| 5,209,826 A | 5/1993 | Ozaki et al. |
| 5,902,458 A | 5/1999 | Sugiura et al. |
| 6,278,005 B1 | 8/2001 | Namiki et al. |

FOREIGN PATENT DOCUMENTS

| CN | 1535970 | * 10/2004 |
| CN | 1535970 A | 10/2004 |

OTHER PUBLICATIONS

Zubrick, The Organic Chem Lab Survival Manual, John Wiley & Sons, 1988, Chapters 20 and 21.*
Zhu et al. STN Document No. 149:362847, Abstract of CN 101254187.*
Nippon Shokuhin Kagaku Kogaku Kaishi (1996), 43(12), 1272-1277.*

* cited by examiner

*Primary Examiner* — Nizal Chandrakumar
(74) *Attorney, Agent, or Firm* — Edwards Wildman Palmer LLP; Peter F. Corless, Esq.; Steven M. Jensen, Esq.

(57) ABSTRACT

The present invention provides a method for preparing sesamin and sesamolin. The method includes the steps of passing a mixed solution of an oil containing sesamin and sesamolin and an aliphatic hydrocarbon solvent through a silica gel column, washing the silica gel column with an aliphatic hydrocarbon solvent, and eluting the sesamin and sesamolin adsorbed by the silica gel column with an eluent selected from the group consisting of methanol, ethanol, acetone and ethyl acetate. The method of the present invention allows a simple and convenient operation, and has excellent purifying effects and high recovery rates. Thus, the method of the present invention has substantial applicability in related industries.

8 Claims, 2 Drawing Sheets

METHOD FOR PREPARING SESAMIN AND SESAMOLIN

BACKGROUND OF THE INVENTION

1. Field of the Invention

The present invention relates to the methods for preparing sesamin and sesamolin, and more particularly, to a method for preparing highly purified sesamin and sesamolin.

2. Description of Related Art

Since the ancient times, sesame has always been regarded as an elixir of health regimens. According to the disclosure of Shen Nong's Herbal Classic, sesame is beneficial to immunization, muscle and brain development, and long-term intake of sesame can lead to rejuvenesce and longevity.

Moreover, it is found from the results obtained from scientific studies conducted in recent years that sesame contains sesamin and sesamolin which have numerous beneficial physiological activities, such as anti-oxidation activity, increasing tocopherol content in vivo, increasing oil metabolism, lowering cholesterol content, prevention of hypertension, improving liver functions and prevention of cancer diseases. These studies showed that sesamin and sesamolin have high applicability in health foods and medicine-related fields.

Although recently some methods for preparing sesamin and sesamolin have been reported, these methods still cannot meet industrial demands in terms of the operating convenience or product purity. For example, U.S. Pat. No. 5,209,826, issued on May 11, 1993, discloses a method for separating sesamin and episesamin, comprising the steps of steam stripping, methylesterification and molecular distillation. However, the separating method requires not only to use expensive equipments, but also to perform a treatment at a temperature as high as 270° C. The product obtained is very prone to quality deterioration. Further, as shown in results of Test 4, the recovery rate of the product was only about 68%, and the purity of the product was only 85%.

Moreover, U.S. Pat. No. 5,902,458, issued on May 11, 1999, discloses a method of separating sesamin and episesamin, comprising the step of steam stripping. In addition, the separating method must, in the presence of an alkali, form precipitate in a solution of water and ethanol for separation. The recovery rate of the product obtained by the method only ranged from 65% to 85%. Further, the method uses a large amount of alkali, which can easily cause contaminations to the environment.

Furthermore, U.S. Pat. No. 6,278,005B1, issued on Aug. 21, 2001, discloses a method for concentrating the concentration of sesamin in sesame oil by using supercritical carbon dioxide. Nevertheless, the goal of the method is only the preparation of sesame oil containing a high concentration of sesamin, instead of preparing sesamin and sesamolin. Further, the method not only uses expensive equipments, but also obtains a total concentration of sesamin and sesamolin of only between 3 to 4%.

Additionally, CN1535970A, published on Oct. 13, 2009, discloses an art for extracting sesamin, comprising the steps of passing sesame oil through neutral aluminum oxide in a cylindrical container, using a fat-soluble solvent to elute oil impurities, collecting a color band containing sesamin from the center of the cylindrical container, and then using a solvent that dissolves sesamin to extract the sesamin from the color band. However, the amounts of the adsorbent and the fat-soluble solvent used by the method are very large. For example, the results in example 2 shows that the ratio of the amounts of the sesame oil and the neutral aluminum oxide used was 1:1, and the amount of the fat-soluble solvent used was 8 to 12 times more than that of the sesame oil (calculated on the basis that the milliliters of eluate obtained in 1 to 1.5 hour is equivalent to the milligrams of the neutral aluminum oxide and the total eluting time of 12 hours). Moreover, the recovery rate of sesamin was only 78.5%, and the method requires performance of the following steps during the operating period: cutting a piece of the neutral aluminum oxide from the center of the cylindrical container, and using >70% ethanol to extract sesamin by performing reflux. The cutting step stops the continuity of operation, which in turn causes inconvenience to operation and lowers the work efficiency. Further, the cutting step is likely to contaminate the work environment by causing solvents to easily evaporate, thereby being detrimental to human health.

In conclusion, an urgent issue of the industry recently to be resolved is to provide a convenient and efficient method for preparing sesamin and sesamolin with high recovery rates and high purity.

SUMMARY OF THE INVENTION

In order to solve the foregoing and other drawbacks, the present invention provides a method for preparing sesamin and sesamolin below.

In an aspect of the present invention, the present invention provides a method for preparing sesamin and sesamolin, comprising the steps of: passing a mixed solution of an oil containing sesamin and sesamolin and a $C_5$-$C_8$ aliphatic hydrocarbon solvent through a silica gel column; washing the silica gel column with the $C_5$-$C_8$ aliphatic hydrocarbon solvent; and eluting the sesamin and sesamolin adsorbed by the silica gel column with an eluting solvent selected from the group consisting of methanol, ethanol, acetone, ethyl acetate and the combination thereof.

In another aspect of the present invention, the present invention provides a method for preparing sesamolin, comprising the steps of: passing a mixed solution of an oil containing sesamin and sesamolin and a $C_5$-$C_8$ aliphatic hydrocarbon solvent through a silica gel column; washing the silica gel column with the $C_5$-$C_8$ aliphatic hydrocarbon solvent; and eluting the sesamolin adsorbed by the silica gel column with n-hexane-ethyl acetate.

In further aspect of the present invention, the present invention provides a method for preparing sesamin, comprising the steps of: passing a mixed solution of an oil containing sesamin and sesamolin and a $C_5$-$C_8$ aliphatic hydrocarbon solvent through a silica gel column; washing the silica gel column with the $C_5$-$C_8$ aliphatic hydrocarbon solvent; and eluting the sesamin adsorbed by the silica gel column with n-hexane-ethyl acetate and ethyl acetate sequentially.

The method according to the above aspect further comprises the step of forming crystals by setting the concentrate of the eluate obtained by eluting the silica gel column.

The method according to the above aspect further comprises the steps of dissolving the crystals in an organic solvent selected from the group consisting of a $C_5$-$C_8$ aliphatic hydrocarbon solvent, methanol, ethanol, acetone, ethyl acetate and the combination thereof, and forming recrystallized crystals by setting the solution.

In the aforesaid method, examples of an oil containing sesamin and sesamolin include sesame oil and oils obtained by using an organic solvent to extract a sesame cake obtained by pressing sesame seeds.

In the aforesaid method, examples of the $C_5$-$C_8$ aliphatic hydrocarbon solvent include pentane, n-hexane, heptane, octane, petroleum ether and a mixture thereof. In a preferred aspect of the present invention, examples of the $C_5$-$C_8$ aliphatic hydrocarbon solvent include n-hexane and petroleum ether.

In yet another aspect of the present invention, the present invention provides a method for preparing sesamin, comprising the steps of: recrystallizing the crystals obtained by the aforesaid method with an organic solvent selected from the group consisting of a $C_5$-$C_8$ aliphatic hydrocarbon solvent, methanol, ethanol, acetone and ethyl acetate.

By using the methods for preparing sesamin and sesamolin provided by the present invention, the operation is simple and convenient. The purification effects are pronounced, and the recovery rates are high. Thus, the method of the present invention has substantial applicability in the related industry.

DETAILED DESCRIPTION OF THE PREFERRED EMBODIMENTS

Figure 1A:
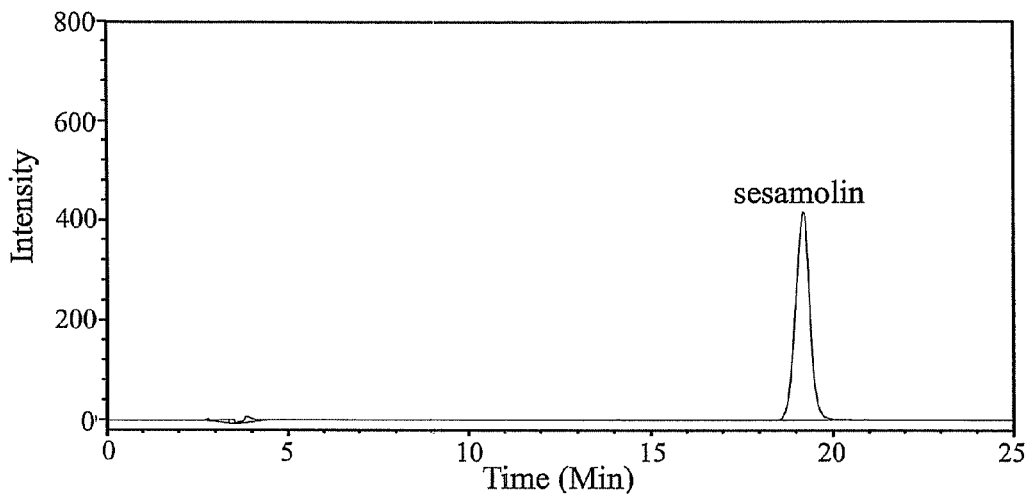
FIG. 1A shows an HPLC chromatogram of fraction-1 obtained by elution using n-hexane-ethyl acetate (9:1) in example 9.

The detailed description of the present invention is illustrated by using specific preferred embodiments below. Persons having ordinary skills in the art can conceive the other advantages and effects of the present invention in light of the disclosure of the specification.

Terminology Used

The term "yield" used herein refers to a percentage calculated by dividing the weight of a product by the weight of a raw material.

The term "content" used herein refers to a percentage calculated by dividing the weight of each component in a product by the weight of the product.

The term "recovery rate" used herein refers to a percentage calculated by dividing the weight of the recovered sesamin and/or sesamolin in a product by the weight of sesamin and/or sesamolin contained in a raw material.

The present invention is specifically illustrated with reference to the following examples. However, it should be noted that the examples only exemplify the present invention, instead of intending to limit the scope of the present invention.

Analytical and Quantitative Methods
1. Generation of a Calibration Curve for Sesamin and Sesamolin Different concentrations of sesamin (ranging from 0.2 to 2 mg/mL) and sesamolin (ranging from 0.2 to 2 mg/mL) were formulated, and were analyzed, respectively, by high performance liquid chromatography (HPLC). The areas obtained under the absorption peaks were plotted against sesamin and sesamolin concentrations to determine a standard curve equation.

2. Quantitative Analyses of Sesamin and Sesamolin

About 1 g of sesame oil or about 0.01 g of refined samples were taken accurately by using an electronic weighing balance. Ethyl acetate (EtOAc) was added to each of the sesame oil or the refined samples to give a 10 mL solution. After thoroughly mixing, 1 mL of the solution was transferred to an eppendorf for centrifuge. Then, an HPLC analysis was performed to generate an HPLC chromatogram. The areas under the absorption peaks in HPLC chromatograms were substituted into the aforesaid standard curve equation to determine the content of each of the compounds (i.e., sesamin and sesamolin) in the samples.

3. HPLC Analytical Conditions
    Column: Waters Polarity™ $dC_{18}$ (5 μm, 250×4.6 mm)
    Mobile phase: 70% methanol (MeOH)
    Flow rate: 1.0 mL/min
    Sample injection volume: 20 μL
    Detector: 290 nm (Spectro Monitor® 3200)

EXAMPLE 1

In 50 mL of n-hexane, 50 g of sesame oil (sesamin content: 0.65%; sesamolin content: 0.31%) was added and thoroughly mixed to obtain a mixed solution. The mixed solution was passed through a column (22 mm×55 mm) packed with silica gel (10 g; 70 to 230 mesh). Oil remained inside the column was eluted by using n-hexane to give an eluate. The eluate was combined with the passed solution, and n-hexane was removed from the oil by evaporation under a reduced pressured. An HPLC analysis was performed on the oil. The obtained analytical results showed that sesamin and sesamolin were not detectable in the oil. This indicated that sesamin and sesamolin present in sesame oil were completely adsorbed by the silica gel, and therefore, they were not removed from the column by eluting with n-hexane. Then, ethyl acetate was used instead to elute the column until the eluate turned colorless. The solvent was removed from the eluate by evaporation under a reduced pressure. The yield was calculated after weighing, and 4.9% was obtained. The eluate after the evaporation was appropriately diluted using ethyl acetate. Then, an HPLC analysis was performed. The total recovery rate of sesamin and sesamolin was calculated, and 97.9% was obtained. Results were shown below in Table 1.

EXAMPLES 2 to 5

The methods performed in examples 2 to 5 were the same as that performed in example 1. However, acetone, methanol, 95% ethanol and n-hexane-ethyl acetate (1:1) were used as eluting solvents, instead of ethyl acetate. The total recovery rates of the obtained sesamin and sesamolin were calculated. They were 95.8%, 95.8%, 89.6% and 95.8% in that order. Results were shown in Table 1.

TABLE 1

Recovery rates of the adsorbed sesamin and sesamolin from silica gel column by elution using different solverts

| | | contents in an eluate(g) | | | recovery |
|---|---|---|---|---|---|
| Example | Eluting solvent | sesamin | sesamolin | Total | rate (%) |
| 1 | ethyl acetate | 0.33 | 0.14 | 0.47 | 97.9 |
| 2 | acetone | 0.32 | 0.14 | 0.46 | 95.8 |
| 3 | methanol | 0.32 | 0.14 | 0.46 | 95.8 |
| 4 | 95% ethanol | 0.29 | 0.14 | 0.43 | 89.6 |
| 5 | n-hexane-ethyl acetate (1:1) | 0.32 | 0.14 | 0.46 | 95.8 |

Note:
Fifty grams of raw material (i.e., sesame oil) contained 0.325 g of sesamin and 0.155 g of sesamolin (total: 0.48 g).

EXAMPLE 6

The method performed in example 6 was the same as that performed in example 1, except that petroleum ether was used to replace n-hexane. The result showed that the total recovery rate of sesamin and sesamolin was 96.4%.

EXAMPLE 7

One hundred grams of silica gel (70 to 230 mesh) was balanced using n-hexane, and were packed in a column (4.4 cm×14 cm). In 500 ml of n-hexane, 500 g of sesame oil was added and thoroughly mixed to obtain a mixture. The mixture was passed through the column, and was eluted with n-hexane until the eluate turned colorless. Then, the eluate was eluted by ethyl acetate until the eluate again turned colorless. The solvent was removed from the eluate by evaporation under a reduced pressure to obtain oil. Then, the oil was set overnight to precipitate the formed crystals. The precipitant was collected by filtration. Oil was removed from the precipitant by washing with n-hexane to obtain 1.7 g of crude crystals. An HPLC analysis was performed. Results showed that the sesamin content was 77.5%, the sesamolin content was 16.8%, and the total content was 94.3%.

EXAMPLE 8

Different solvents such as ethyl acetate, acetone, methanol and 95% ethanol were each slowly and dropwisely added to 10 g of the crude crystals prepared according example 7 at 50° C., until the crude crystals were completely dissolved to obtain a solution. Each solution was set at room temperature to cool for 2 days to obtain a precipitated, recrystallized product. The crystals were collected. The solvents were removed from the crystals by evaporation under a reduced pressure to obtain a final product as white crystals. The HPLC analysis were performed. Results were shown below in Table 2, wherein the sesamin contents were all above 92%.

TABLE 2

Sesamin and sesamolin contents in the recrystallized samples obtained by recrystallization using various solvents

| | Content (%) | | |
|---|---|---|---|
| Sample | sesamin | sesamotin | Total |
| Crude crystals | 77.5 | 16.8 | 94.3 |
| recrystallized from ethyl acetate | 94.0 | 2.0 | 96.0 |
| recrystallized from acetone | 93.4 | 3.1 | 96.5 |
| recrystallized from methanol | 94.3 | 3.6 | 97.9 |
| recrystallized from 95% ethanol | 92.0 | 4.3 | 96.3 |

EXAMPLE 9

Figure 1B:
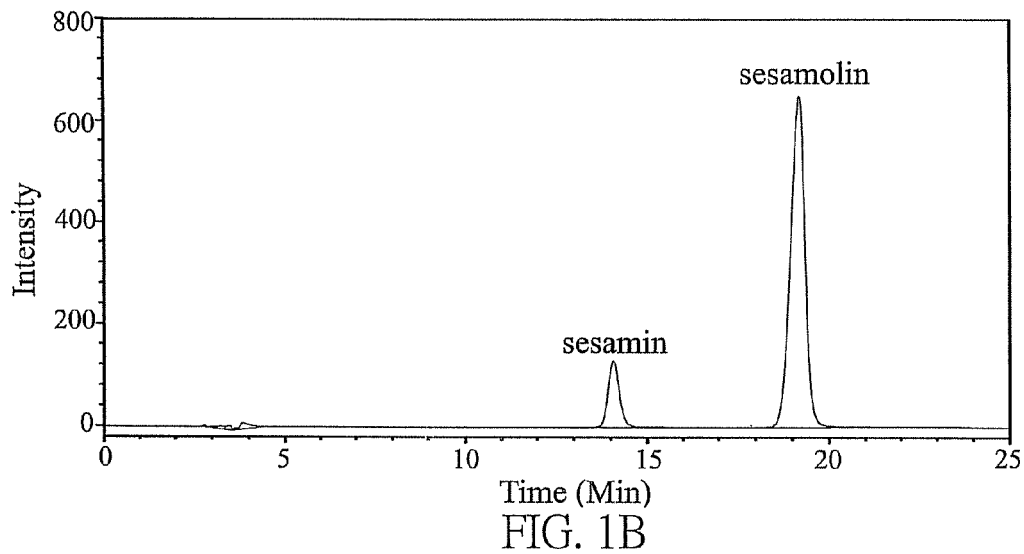
FIG. 1B shows an HPLC chromatogram of fraction-2 obtained by elution using n-hexane-ethyl acetate (9:1) in example 9.
Figure 1C:
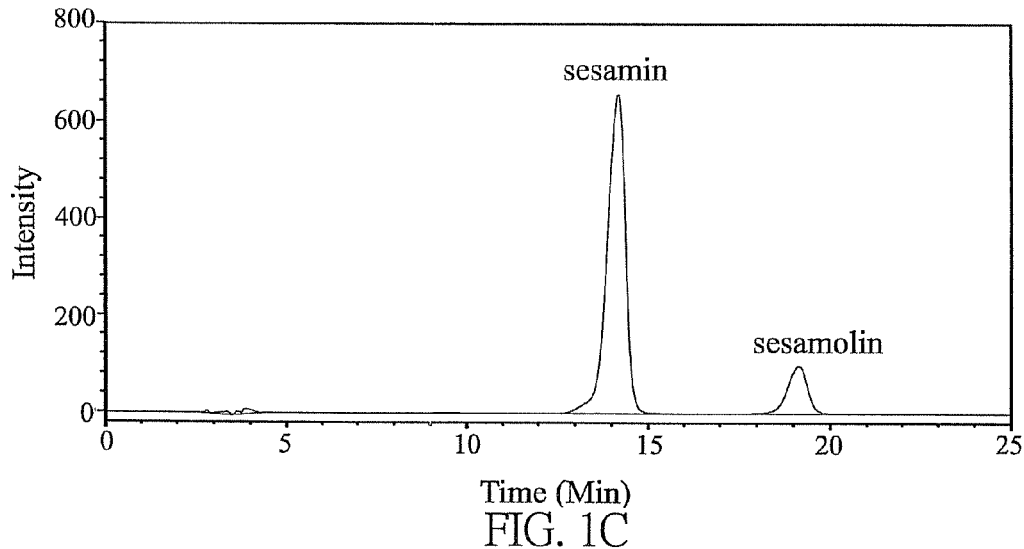
FIG. 1C shows an HPLC chromatogram obtained by elution using ethyl acetate in example 9.
Figure 2:
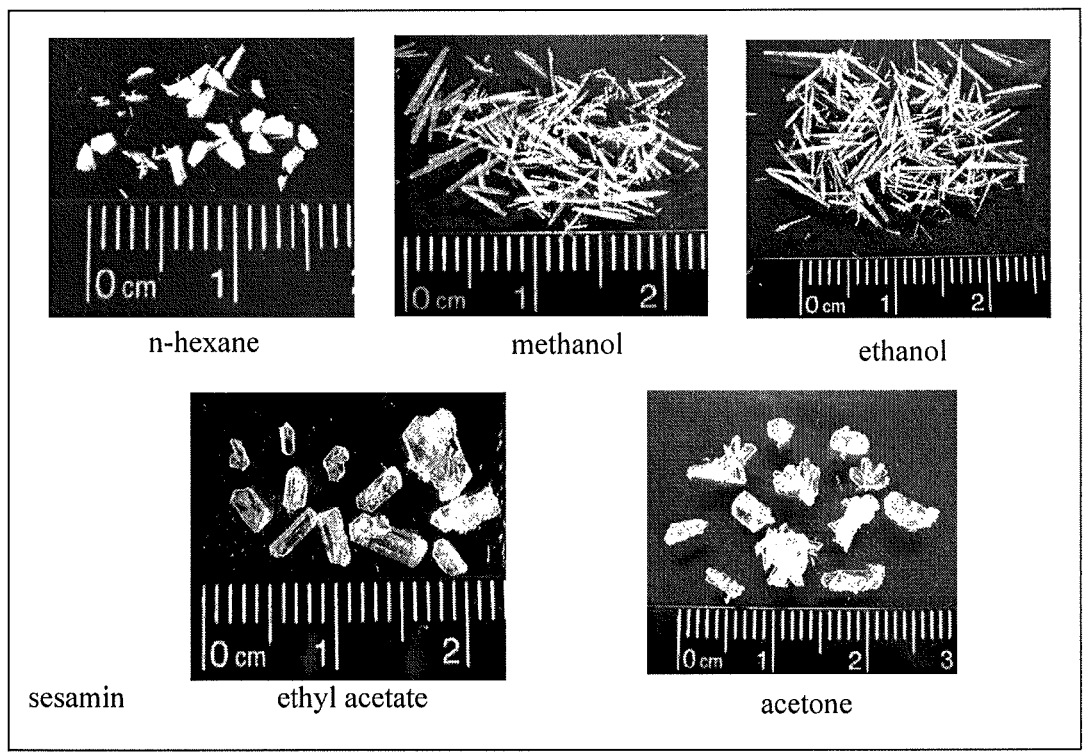
FIG. 2 shows photos of the recrystallized crystals obtained by recrystallization using different solvents in example 9.
Figure 2:
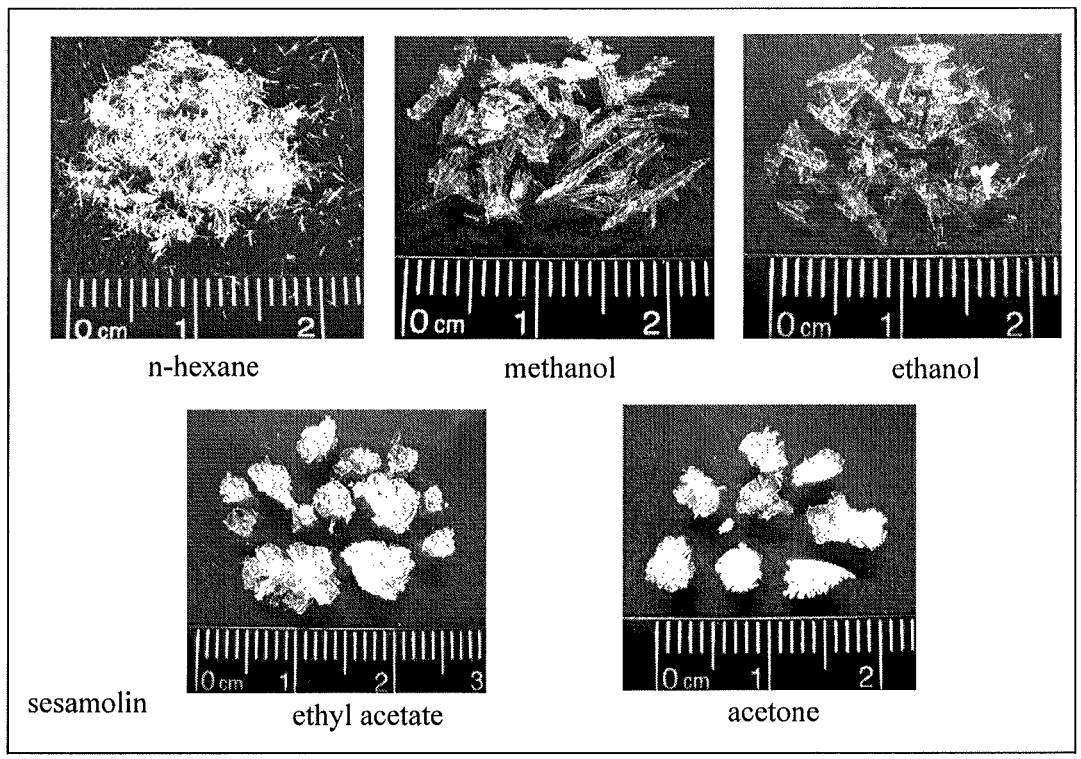

One hundred grams of silica gel (70 to 230 mesh) was balanced using n-hexane, and were packed in a column (4.4 cm×14 cm). In 2000 ml of n-hexane, 500 g of sesame oil was added and thoroughly mixed to obtain a mixture. The mixture was passed through the silica gel column. The unabsorbed oil was sufficiently eluted with n-hexane. Then, elution was performed by using solvents in the order of n-hexane-ethyl acetate (9:1), ethyl acetate and acetone. When n-hexane-ethyl acetate (9:1) was used for elution, each 500 mL of eluate was collected as a "fraction", and a total of 2 fractions (respectively called "fraction-1" and "fraction-2") were collected. Subsequently, when 1 L of ethyl acetate and 1 L of acetone were used for elution, ethyl acetate and acetone fractions were respectively collected. Then, the solvents were removed from each of the aforesaid fractions by evaporation under a reduced pressure and weighed. Yields were calculated for all fractions. The HPLC analyses were performed, and contents, recovery amounts and recovery rates of sesamin and sesamolin in all fractions were calculated. After the removal of solvents, fraction-1 and fraction-2 concentrates were set to crystallize. The residual oil in the crystals was removed by washing with n-hexane, thereby the crystals with sesamolin as the major component were obtained (see FIGS. 1A and 1B). After removal of solvents, the ethyl acetate fraction with sesamin as the major component were obtained (see FIG. 1C). The amount of acetone fraction concentrate was scarce. The yield of the acetone fraction was only 0.2%, and no sesamin or sesamolin were detected therein. The aforesaid results were shown in Table 3 below, wherein elution with n-hexane-ethyl acetate (9:1) could give a fraction containing a high content of sesamolin with recovery rate of 80.9%, and elution with ethyl acetate could give a fraction containing a high content of sesamin with a recovery rate of 96.3%. Subsequently, the obtained sesamin and sesamolin crystals were recrystallized using different solvents (i.e., n-hexane, ethyl acetate, acetone, methanol and 95% ethanol), respectively. The obtained crystals were shown in Table 2, wherein the purities of the recrystallized crystals were all over 95%.

TABLE 3

Results of separating sesamin and sesamolin from sesame oil using silica gel column.

| fraction[1] | yield (%) | recovery amount(mg) | | recovery rate(%) | |
|---|---|---|---|---|---|
| | | sesamin | sesamolin | sesamin | sesamolin |
| n-hexane | 95.0 | —[3] | — | — | — |
| n-hexane-ethyl acetate (9:1)[2] (fraction-1) | 1.0 | — | 682.2 | — | 30.5 |
| n-hexane-ethyl acetate (9:1)[2] (fraction -2) | 0.7 | 52.6 | 1127.3 | 1.9 | 50.4 |
| ethyl acetate fraction | 1.3 | 2615.8 | 369.5 | 96.3 | 16.5 |
| acetone fraction | 0.2 | — | — | — | — |
| Total | 98.2 | 2668.4 | 2179.0 | 98.2 | 97.4 |

Note:
Five hundred grams of raw material (i.e., sesame oil) contained 2716 mg of sesamin and 2239 mg of sesamolin (Total: 4955 mg).
[1]Unless specified, the term "fraction" used herein refers to a fraction obtained by elution using a 1 L solvent.
[2]When n-hexane-ethyl acetate (9:1) was used for elution, each 500 mL of eluate was collected as a fraction, and a total of 2 fractions (respectively called "fraction-1" and "fraction-2") were collected.
[3]The symbol "—" indicated undetectable.

EXAMPLE 10

Five-hundred grams of sesame cake obtained by pressing sesame seeds was grounded, and 2000 ml n-hexane was added, the mixture was stirred for 2 hours at 60° C. for extraction, the mixture was suction filtered to obtain the filtrate. The same steps were performed on the filter cake for re-extraction. The extracts obtained from the two extractions were combined, and the combined extract was evaporated under a reduced pressure, thereby obtaining 43.6 g of oil. An HPLC analysis was performed, and the result showed that the obtained oil contained 0.48% of sesamin and 0.32% of sesamolin. Forty-grams of oil were mixed with 50 ml of n-hexane to obtain a mixture. The mixture was passed through a silica gel (10 g; 70 to 230 mesh) column (22 mm×55 mm). Residual oil was removed from the column by elution using n-hexane, until the eluate turned colorless. The n-hexane eluate was mixed with the passed solution, and the solvent was removed from the combined solution by evaporation under a reduced pressure, thereby obtaining 37.8 g of oil. An HPLC analysis was performed, and the result showed that sesamin and sesamolin were undetectable. Subsequently, the adsorbed sesamin and sesamolin were eluted with ethyl acetate until the eluate turned colorless. The solvent was removed from the eluate by evaporation under a reduced pressured, and 1.72 g of oily substance was obtained. An HPLC analysis was performed, and the result showed that there were 10.8% of sesamin and 7.12% of sesamolin in the oily substance. The total recovery rate of sesamin and sesamolin were calculated as 96.3%.

The present invention has been described using exemplary preferred embodiments. However, it is to be understood that the scope of the invention is not limited to the disclosed arrangements. The scope of the claims, therefore, should be according the broadest interpretation, so as to encompass all such modifications and similar arrangements.

The invention claimed is:

1. A method for preparing sesamin and sesamolin, comprising the steps of:
    passing a mixed solution of sesame oil and a $C_5$-$C_8$ aliphatic hydrocarbon solvent through a silica gel column;
    washing the silica gel column with the $C_5$-$C_8$ aliphatic hydrocarbon solvent; and
    eluting sesamin and sesamolin adsorbed by the silica gel column with a solvent selected from the group consisting of methanol, ethanol, acetone, ethyl acetate, and a combination thereof.

2. The method of claim 1, wherein the sesame oil is an oil obtained by using an organic solvent to extract a sesame cake obtained by pressing sesame seeds.

3. The method of claim 1, wherein the $C_5$-$C_8$ aliphatic hydrocarbon solvent is one selected from the group consisting of pentane, n-hexane, heptane, octane, petroleum ether and a combination thereof.

4. The method of claim 1, further comprising the step of forming crystals by setting a concentrate of an eluate obtained by eluting the silica gel column.

5. The method of claim 4, further comprising the steps of dissolving the crystals in an organic solvent selected from the group consisting of a $C_5$-$C_8$ aliphatic hydrocarbon solvent, methanol, ethanol, acetone, ethyl acetate and a combination thereof, and forming recrystallized crystals by setting.

6. A method for preparing sesamin, comprising the step of further recrystallizing the crystals of claim 4 with an organic solvent selected from the group consisting of a $C_5$-$C_8$ aliphatic hydrocarbon solvent, methanol, ethanol, acetone, ethyl acetate and a combination thereof.

7. A method for preparing sesamolin, comprising the steps of:
    passing a mixed solution of sesame oil and a $C_5$-$C_8$ aliphatic hydrocarbon solvent through a silica gel column;
    washing the silica gel column with the $C_5$-$C_8$ aliphatic hydrocarbon solvent; and
    eluting sesamolin adsorbed by the silica gel column by elution using n-hexane-ethyl acetate.

8. A method for preparing sesamin, comprising the steps of:
    passing a mixed solution of sesame oil and a $C_5$-$C_8$ aliphatic hydrocarbon solvent through a silica gel column;
    washing the silica gel column with the $C_5$-$C_8$ aliphatic hydrocarbon solvent; and
    eluting sesamin adsorbed by the silica gel column with n-hexane-ethyl acetate and ethyl acetate sequentially.

* * * * *